United States Patent [19]

Neumann et al.

[11] Patent Number: 4,990,680

[45] Date of Patent: Feb. 5, 1991

[54] PROCESS FOR THE PREPARATION OF 2,4-DIHYDROXYBENZOPHENONE

[75] Inventors: Peter Neumann, Mannheim; Alexander Aumueller, Deidesheim, both of Fed. Rep. of Germany

[73] Assignee: BASF Aktiengesellschaft, Ludwigshafen, Fed. Rep. of Germany

[21] Appl. No.: 463,365

[22] Filed: Jan. 11, 1990

[30] Foreign Application Priority Data

Feb. 14, 1989 [DE] Fed. Rep. of Germany ....... 3904371

[51] Int. Cl.$^5$ ............................................. C07C 45/45
[52] U.S. Cl. ................................................... 568/322
[58] Field of Search ........................................ 568/322

[56] References Cited

U.S. PATENT DOCUMENTS 4,568,429  2/1986  Liu ....................................... 568/322

FOREIGN PATENT DOCUMENTS 0032275  7/1981  European Pat. Off. ............ 568/322

Primary Examiner—James H. Reamer
Attorney, Agent, or Firm—Oblon, Spivak, McClelland, Maier & Neustadt

[57] ABSTRACT

A process for the preparation of 2,4-dihydroxybenzophenone by reacting resorcinol with benzotrichloride in water, wherein the reaction mixture contains a surfactant or a dispersing or emulsifying agent in a concentration of from 0.05 to 5%, by weight of the water.

The product is obtained in high yield and good purity.

13 Claims, No Drawings

PROCESS FOR THE PREPARATION OF 2,4-DIHYDROXYBENZOPHENONE 2,4-Dihydroxybenzophenone is a commercially significant UV absorber useful for protecting organic matter from damage due to sunlight and as a cosmetic sunguard.

It has been known for a number of years that 2,4-dihydroxybenzophenone can be prepared by reacting benzotrichloride with resorcinol in water (*German Chemical Society Reports* 27, p. 1998 (1894)). Drawbacks of this process are the poor yield and the formation of dark-colored by-products making high-cost purification necessary. DE-OS 2,208,970 claims a process for the manufacture of 2,4-dihydroxybenozophenone in an organic solvent mixture. The disadvantage of this process is that the constituent solvents must be recovered by complicated procedures.

Another industrially uneconomical process is that described in DE-OS 2,451,037, in which hydrogen fluoride is used as solvent.

The prior art also discloses the use of mixtures of water and organic solvents such as methanol, acetic acid, dioxane and/or propanol (cf. DD-PS 93,546, DE-OS 2,010,535, US-PS 3,769,349). Apart from giving poor yields, these processes suffer from the drawback that solvent recovery is possible only by carrying out laborious measures or that the waste water is highly contaminated by organic solvent residues.

It is an object of the present invention to provide a process for the preparation of 2,4-dihydroxybenzophenone which can be readily carried out on an industrial scale without having an adverse effect on the environment.

The invention relates to a process for the preparation of 2,4-dihydroxybenzophenone by reacting resorcinol with benzotrichloride in water, which is characterized in that the reaction mixture contains a surfactant or a dispersing or emulsifying agent in a concentration of from 0.05% to 5%, by weight of the water.

We have found that, surprisingly, even a very small addition of said agents to the reaction mixture comprising benzotrichloride and resorcinol in water leads to a high yield of pure product.

Suitable auxiliaries are surfactants (tensides), dispersants or emulsifiers. These may be non-ionic or ionic and of low or high molecular weight. Examples thereof are:

$C_8$–$C_{20}$-alkenols, $C_8$–$C_{20}$-alkanols, polyvinylalcohols, fatty acids, fatty acid esters, adducts of ethylene oxide with $C_1$–$C_{20}$-alkylphenols, with $C_1$–$C_{20}$-alkanols, with $C_2$–$C_8$-alkanediols, with $C_2$–$C_8$-alkenediols, with $C_3$–$C_8$-alkanetriols, with $C_{10}$–$C_{25}$-alkanoic or $C_{10}$–$C_{25}$-alkenoic acids, with amides of $C_{10}$–$C_{25}$-alkanoic or $C_{10}$–$C_{25}$-alkenoic acids, or with aliphatic or cycloaliphatic amines, acidic phosphoric acid esters or sulfuric acid half-esters of said alkenols, alkanols and ethylene oxide adducts, esters of phosphorous acid, phosphonates, phosphinates, alkylnaphthalenesulfonic acids, sulfosuccinic acid esters, $C_5$–$C_{20}$-alkylbenzenesulfonic acids, polystyrenesulfonic acid, $C_{10}$–$C_{20}$-alkanesulfonic acids, $C_{10}$–$C_{20}$-alkenesulfonic acids, mono-$C_8$–$C_{20}$-alkyl-tri$C_1$–$C_4$-alkylammonium -$C_{20}$-alkyl-tri-$C_1$–$C_4$-alkylammonium salts, di-$C_8$–$C_{20}$-alkyl-di-$C_1$–$C_4$-alkylammonium salts and $C_{10}$–$C_{20}$-alkylpyridinium salts.

Examples of specific compounds are:

Oleyl alcohol, polyethylene glycol (av. mol. wt. 200, 400, 1000), sulfuric acid half-esters of the EO adduct with $C_9$-alkylphenol, sulfuric acid half-esters of the EO adduct with $C_{16}$–$C_{19}$-oxoalcohols and $C_{12}$–$C_{14}$-alkanols, dodecylbenzenesulfonic acid, $C_{14}$-alkylsulfonic acid, $C_{17}$-alkylsulfonic acid, fatty alcohol sulfates containing 12, 14 or 18 carbon atoms, EO adducts with alkanols containing 12, 14, 15, 16 or 18 carbon atoms, EO adducts with hexyl-, nonyl-and dodecyl-phenols, polyglycol stearates, polyglycol oleates, polyglycol dioleates, oleic amide polyglycol ether, coconut oil fatty acid monoethanolamide, coconut oil fatty acid diethanolamide, stearyl trimethylammonium salts, palmityl trimethylammonium salts, distearyl dimethylammonium salts, dodecylbenzyl dimethylammonium salts, stearyl pyridinium and dodecyl pyridinium salts.

The acidic phosphoric acid esters and the sulfuric acid half-esters (sulfates) are usually used in the form of soluble salts such as alkali metal or amine salts, the ammonium salts in the form of bromides, sulfates, acetates and, in particular, chlorides.

Preferred auxiliaries are saturated or unsaturated fatty alcohols (alkanols), EO adducts with alkylphenols, fatty acids in the form of salts, polyethylene glycol, sulfuric acid half-esters of EO adducts with alkylphenols, fatty acid esters, alkylbenzenesulfonic acids or mixtures of said auxiliaries.

The process of the invention is illustrated by the following Examples.

EXAMPLE 1

1,000 ml of water are placed in a vessel having a capacity of 2 liters. 220 g (2.0 moles) of resorcinol are added with stirring. When this has dissolved, 2.12 ml (2.5 g) of cis-9-octadecen-1-ol (oleyl alcohol) are added. 294 ml (2.0 moles) of benzotrichloride are added dropwise over 1.5 hours. A strongly exothermic reaction takes place and this addition must be carried out at such a rate that the temperature remains in the range of 40°–50° C.

When all of the benzotrichloride has been added, the reaction mixture is heated at 70° C. for 1 hour, after which the heater is switched off and the product is filtered off in vacuo and washed with hot water.

After drying in vacuo at 80° C. there are obtained 420 g (98% of theory) of crude 2,4-dihydroxybenzophenone as a yellowish orange powder melting at 139°–140° C.

If 750 ml of water are used instead of 1000 ml, the same result is obtained.

EXAMPLE 2 to 12

Example 1 is repeated except that the auxiliaries listed in column 2 of the Table below are used in the amounts given in column 3. The respective yield and melting point of the product obtained are given in columns 4 and 5 of the Table.

In Examples 9 to 12 a 4 liter vessel is used.

TABLE
Preparation of 2,4-dihydroxybenzophenone

| Ex. | Auxiliary | Amount [g] | Yield [% theory] | M.P. [° C.] |
|---|---|---|---|---|
| 2 | oleyl alcohol | 5.00 | 96 | 139–141 |
| 3 | 1-heptanol | 1.73 | 96 | 136–138 |
| 4 | 1-dodecanol | 5.00 | 97 | 136–138 |
| 5 | ethylene glycol | 2.24 | 94 | 136–138 |
| 6 | 1,3-propanediol | 2.50 | 93 | 138–140 |
| 7 | polyethylene glycol of | 5.00 | 97 | 134–136 |

TABLE-continued

Preparation of 2,4-dihydroxybenzophenone

| Ex. | Auxiliary | Amount [g] | Yield [% theory] | M.P. [°C.] |
|---|---|---|---|---|
| 8 | polyethylene glycol of average mol. wt. 200 | 10.00 | 96 | 138-140 |
| 9 | *sulfuric acid half-ester of EO adduct with C9-alkylphenol | 3.00 | 95 | 139-141 |
| 10 | *sulfuric acid half-ester of EO adduct with C9-alkylphenol | 6.25 | 93 | 140-141 |
| 11 | *alkanolamine salt of dodecylbenzenesulfonic acid | 12.50 | 95 | 135-137 |
| 12 | *sulfuric acid half-ester of EO adduct with C16–C19-oxoalcohol mixture | 12.50 | 94 | 137-139 |

*2 liters of water used as solvent

We claim:

1. A process for the preparation of 2,4-dihydroxybenzophenone comprising reacting resorcinol with benzotrichloride in water, wherein the reaction mixture contains a surfactant or a dispersing or emulsifying agent in a concentration of from 0.05 to 5%, by weight of the water, wherein said surfactant or dispersing or emulsifying agent are $C_8$–$C_{20}$-alkenols, $C_8$–$C_{20}$-alkanols, polyvinylalcohols, fatty acids, fatty acid esters, adducts of ethylene oxide with $C_1$–$C_{20}$-alkylphenols, with $C_1$–$C_{20}$-alkanols, with $C_2$–$C_8$-alkanedoils, with $C_2$–$C_8$-alkenediols, with $C_3$–$C_8$-alkanetriols, with $C_{10}$–$C_{25}$-alkanoic or $C_{10}$–$C_{25}$-alkenoic acids, with amides of $C_{10}$–$C_{25}$-alkanoic or $C_{10}$–$C_{25}$-alkenoic acids, or with aliphatic or cycloaliphatic amines, acidic phosphoric acid esters or sulfuric acid half-esters of said alkenols, alkanols and ethylene oxide adducts, esters of phosphorous acid, phosphonates, phosphinates, alkylnaphthalenesulfonic acids, sulfosuccinic acid esters, $C_5$–$C_{20}$-alkylbenzenesulfonic acids, polystyrenesulfonic acid, $C_{10}$–$C_{20}$-alkanesulfonic acids, $C_{10}$–$C_{20}$-alkenesulfonic acids, mono-$C_6$–$C_{20}$-alkyl-tri-$C_1$–$C_4$-alkylammonium salts, di-$C_8$–$C_{20}$-alkyl-di-$C_1$–$C_4$-alkylammonium salts or $C_{10}$–$C_{20}$-alkylpyridinium salts.

2. A process as claimed in claim 1, wherein the concentration of said surfactant or dispersing or emulsifying agent is from 0.05 to 2%, by weight of the water.

3. A process as claimed in claim 1, wherein said surfactant or dispersing or emulsifying agent is a saturated or unsaturated fatty alcohol, an EO adduct with alkylphenol, a fatty acid in the form of a salt, a polyethylene glycol, a sulfuric acid half-ester of an EO adduct with alkylphenol, a fatty acid ester, an alkylbenzenesulfonic acid or a mixture of these.

4. A process as claimed in claim 1, wherein said surfactant or dispersing or emulsifying agent is oleyl alcohol, polyethylene glycol (av. mol. wt. 200, 400, 1000), sulfuric acid half-esters of the EO adduct with $C_9$-alkylphenol, sulfuric acid half-esters of the EO adduct with $C_{16}$–$C_{19}$-oxoalcohols, and $C_{12}$–$C_{14}$-alkanols, dodecylbenzenesulfonic acid, $C_{14}$-alkylsulfonic acid, $C_{17}$-alkylsulfonic acid, fatty alcohol sulfates containing 12, 14 or 18 carbon atoms, EO adducts with alkanols containing 12, 14, 15, 16 or 18 carbon atoms, EO adducts with hexyl-, nonyl- and dodecyl-phenols, polyglycol stearates, polyglycol oleates, polyglycol dioleates, oleic amide polyglycol ether, coconut oil fatty acid monoethanolamide, coconut oil fatty acid diethanolamide, stearyl trimethylammonium salts, palmityl triethylammonium salts, distearyl dimethylammonium salts, dodecylbenzyl dimethylammonium salts, stearyl pyridinium salt, dodecyl pyridinium salt, or said acidic phosphoric acid esters and sulfuric acid half-esters in the form of soluble alkali metal, amine or ammonium salts, the ammonium salts being in the form of bromides, sulfates, acetates or chlorides.

5. A process as claimed in claim 1, wherein said surfactant or dispersing or emulsifying agent is oleyl alcohol.

6. A process as claimed in claim 1, wherein said surfactant or dispersing or emulsifying agent is 1-heptanol.

7. A process as claimed in claim 1, wherein said surfactant or dispersing or emulsifying agent is 1-dodecanol.

8. A process as claimed in claim 1, wherein said surfactant or dispersing or emulsifying agent is ethylene glycol.

9. A process as claimed in claim 1, wherein said surfactant or dispersing or emulsifying agent is 1,3-propanediol.

10. A process as claimed in claim 1, wherein said surfactant or dispersing or emulsifying agent is polyethylene glycol of average mol. wt. 200.

11. A process as claimed in claim 1, wherein said surfactant or dispersing or emulsifying agent is sulfuric acid half-ester of EO adduct with $C_9$-alkylphenol.

12. A process as claimed in claim 1, wherein said surfactant or dispersing or emulsifying agent is alkanolamine salt of dodecylbenzenesulfonic acid.

13. A process as claimed in claim 1, wherein said surfactant or dispersing or emulsifying agent is sulfuric acid half-ester of EO adduct with $C_{16}$–$C_{19}$-oxoalcohol mixture.

* * * * *